United States Patent
Zhu et al.

(10) Patent No.: US 7,141,694 B2
(45) Date of Patent: Nov. 28, 2006

(54) ENZYMATIC RESOLUTION OF ARYL AND THIO-SUBSTITUTED ACIDS

(75) Inventors: Jingyang Zhu, Jamesville, NY (US); Shannon X. Zhao, East Syracuse, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 501 days.

(21) Appl. No.: 10/625,403

(22) Filed: Jul. 23, 2003

(65) Prior Publication Data

US 2004/0077061 A1    Apr. 22, 2004

Related U.S. Application Data

(62) Division of application No. 09/946,722, filed on Sep. 5, 2001, now Pat. No. 6,620,600.

(60) Provisional application No. 60/233,193, filed on Sep. 15, 2000.

(51) Int. Cl.
C07C 69/76     (2006.01)
C07C 69/96     (2006.01)

(52) U.S. Cl. .................. 560/51; 560/126; 560/174

(58) Field of Classification Search .............. 560/51, 560/126, 174
See application file for complete search history.

(56) References Cited

U.S. PATENT DOCUMENTS

| | | |
|---|---|---|
| 5,508,272 A | 4/1996 | Robl |
| 5,552,397 A | 9/1996 | Karanewsky et al. |
| 6,080,881 A | 6/2000 | Pietro et al. |
| 6,103,931 A | 8/2000 | Allegrini et al. |
| 6,133,002 A | 10/2000 | Boesten et al. |
| 6,140,088 A | 10/2000 | Hanson et al. |
| 6,162,913 A | 12/2000 | Moniot et al. |
| 6,166,227 A | 12/2000 | Godfrey, Jr. et al. |
| 6,174,707 B1 | 1/2001 | Taoka et al. |
| 6,174,711 B1 | 1/2001 | Tanaka et al. |
| 6,222,052 B1 | 4/2001 | Boesten et al. |
| 6,222,062 B1 * | 4/2001 | Anderson et al. ........... 560/174 |
| 6,248,882 B1 | 6/2001 | Godfrey, Jr. et al. |
| 6,261,810 B1 | 7/2001 | Patel et al. |
| 6,300,503 B1 | 10/2001 | Rongione et al. |
| 6,348,618 B1 * | 2/2002 | Anderson et al. ........... 560/174 |

FOREIGN PATENT DOCUMENTS

| | | |
|---|---|---|
| EP | 0905257 A1 | 3/1999 |
| EP | 0919630 A1 | 6/1999 |
| JP | 2000-23693 | 1/2000 |
| WO | WO99/35145 | 7/1999 |

OTHER PUBLICATIONS

Mignani et al., Tetrahedron Letters, vol. 28, No. 45, pp. 5505-5508, 1987.
Ranu et al., J. Chem. Soc. Perkin, Trans 1, 1992, p. 365-368.
Brandstrom et al., Acta Chem. Scand. 23, (1969) No. 6, pp. 2204-2205.
Durst et al., J. Org. Chem., J. Org. Chem., vol. 39, No. 22, 1974, pp. 3271-3273.

* cited by examiner

*Primary Examiner*—Herbert J. Lilling
(74) *Attorney, Agent, or Firm*—Burton Rodney

(57) ABSTRACT

Provided is a method of resolving a racemic mixture of a compound of formula I to obtain a desired enantiomer:

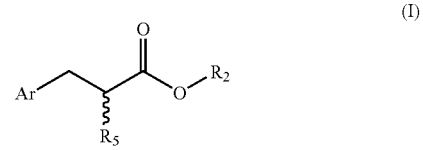

(I)

wherein Ar is $C_6$ or $C_{10}$ aromatic group that can be substituted with H, $C_1$ to $C_6$ alkyl, trifluoromethyl or halo, $R_5$ is halo or —S—$R_1$, wherein $R_1$ is H or acetyl, and $R_2$ is H or $C_1$ to $C_6$ alkyl, the method comprising: reacting a compound of formula I wherein the compound is an ester whereby $R_2$ is $C_1$ to $C_6$ alkyl with a lipase derived from *Mucor meihei* to stereoselectively hydrolyze the ester bond to produce an acid; and isolating the acid, wherein the reaction is conducted in a solvent comprising 80% to 98% v/v % organic phase and a residue of water phase (which can be buffered).

10 Claims, No Drawings

ENZYMATIC RESOLUTION OF ARYL AND THIO-SUBSTITUTED ACIDS

This application is a Divisional of Ser. No. 09/946,722 filed Sep. 5, 2001, now U.S. Pat. No. 6,620,600 which claims priority from Provisional Ser. No. 60/233,193 filed Sep. 15, 2000.

BACKGROUND OF THE INVENTION

Over the last several years compounds have been reported in the patent and technical literature as possessing angiotensin converting enzyme (ACE) inhibitory activity or neutral endopeptidase (EC 3.4.24.11; NEP) inhibitory activity. Additional compounds have been identified that possess both inhibitory activities. These dual inhibitor compounds are of interest as cardiovascular agents particularly in the treatment of hypertension, congestive heart failure, and renal disease. These compounds are also referred to as vasopeptidase, dual metalloprotease, NEP/ACE, or ACE/NEP inhibitors.

Omapatrilat is such a vasopeptidase inhibitor which is currently undergoing clinical evaluation. Omapatrilat has the chemical name [4S-[4α(R*),7α,10aβ]]-octahydro-4-[(2-mercapto-1-oxo-3-phenylpropyl)amino]-5-oxo-7H-pyrido[2,1-b][1,3]thiazepine-7-carboxylic acid and the structural formula:

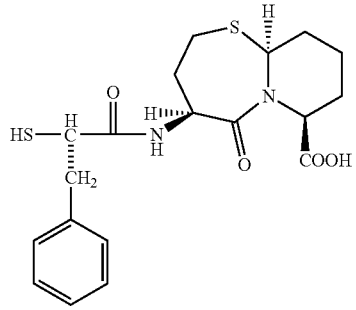

Omapatrilat

Omapatrilat, its preparation, and its use in treating cardiovascular disease are disclosed by Robl in U.S. Pat. No. 5,508,272.

Gemopatrilat having the chemical name [S—(R*,R*)]-hexahydro-6-[(2mercapto-1-oxo-3-phenylpropyl)amino]-2,2-dimethyl-7-oxo-1H-azepine-1-acetic acid is another vasopeptidase inhibitor which is currently undergoing clinical evaluation. This compound has the structural formula:

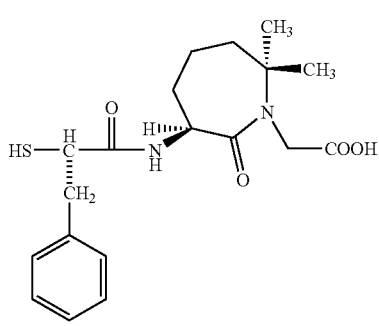

Gemopatrilat

This compound, its preparation, and its use in treating cardiovascular diseases are disclosed by Karanewsky et al. in U.S. Pat. No. 5,552,397. Processes for preparing vasopeptidase inhibitors including omapatrilat and gemopatrilat are disclosed by Kronenthal et al in WO 99/35145 and processes for preparing omapatrilat and omapatrilat intermediates are disclosed by Godfrey et al in U.S. Pat. Nos. 6,166,227 and 6,248,882, by Moniot et al. in U.S. Pat. No. 6,162,913, by Hanson et al. in U.S. Pat. No. 6,140,088, and by Patel et al. in WO 00/14265. Other processes for preparing omapatrilat intermediates are disclosed by Taoka et al. in U.S. Pat. No. 6,174,707, by Tanaka et al. in U.S. Pat. No. 6,174,711, and by Boesten et al. in U.S. Pat. Nos. 6,133,002 and 6,222,052.

Methods for producing thio aryl and thio-substituted acid moieties such as those incorporated into such vasopeptidase inhibitors are costly. For example, unnatural amino acids such as D-phenylalanine can be converted to α-halides with retention of configuration (using diazotization conditions) and stereospecifically inverted to an appropriate thio-containing intermediate. However, the cost of enantiomerically pure D-phenylalanine is high. Methods are needed that produce the desired enantiomer from inexpensive starting materials.

Methods of using lipases in aqueous buffers to stereoselectively produce a desired acid from 2-acetylthio-3-phenylpropionic acid ester have been described in JP2000-23693A. However, usable e.e. values are not obtained with a particularly desirable enzyme, the lipase obtained from *Mucor Meihei* and marketed by Novo Nordisk Biotech, Inc. (soon to be Novozymes, Inc.) as Lipozyme IM. An improved method is needed to obtain higher e.e. values and to allow the reuse of the enzyme.

Furthermore, the art contains no detail on how to purify the crude product from stereoselection using the lipozyme IM enzyme to a product that would be suitable for pharmaceutical use (>98.5% ee). A method is needed for this.

Also, there is no demonstration of how to reuse the recovered unreacted ester. If the recovered ester is not reused, then the cost will be prohibitive. Methods for the reuse of the unreacted ester are also desired.

SUMMARY OF THE INVENTION

The invention provides a method of resolving a racemic mixture of a compound of formula I to obtain a desired enantiomer:

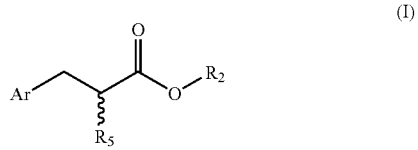

wherein Ar is $C_6$ or $C_{10}$ aromatic group that can be substituted with H, $C_1$ to $C_6$ alkyl, trifluoromethyl or halo, $R_5$ is halo or —S—$R_1$, wherein $R_1$ is H or acetyl, and $R_2$ is H or $C_1$ to $C_6$ alkyl, the method comprising: reacting a compound of formula I wherein the compound is an ester whereby $R_2$ is $C_1$ to $C_6$ alkyl with a lipase derived from *Mucor meihei* to stereoselectively hydrolyze the ester bond to produce an acid; and isolating the acid, wherein the reaction is conducted in a solvent comprising 80% to 98% v/v % organic phase and a residue of water phase (which can be buffered).

Another aspect of the invention provides a method of stereoselectively producing a desired enantiomer of a compound of formula I:

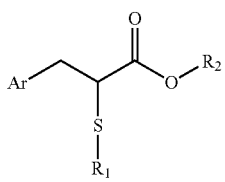

wherein Ar is $C_6$ or $C_{10}$ aromatic group that can be substituted with H, $C_1$ to $C_6$ alkyl, trifluoromethyl or halo, $R_1$ is H or acetyl, and $R_2$ is H or $C_1$ to $C_6$ alkyl, the method comprising: reacting Ar—$CH_2$—X, where X is a leaving group, with $R_4$—C(O)—$CH_2$—C(O)O—$R_{2*}$, wherein $R_{2*}$ and $R_4$ are independently $C_1$ to $C_6$ alkyl; reacting a resulting compound of formula II:

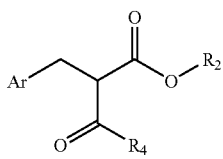

with a halogenating agent which comprises an N-halo substituted amide, N-halosubstituted imide, N-halosubstituted thioamide, or N-halosubstituted thioimide as the halogenating moiety to produce, with or without an additional hydrolysis of the ester, a compound of formula III:

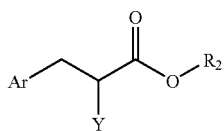

wherein Y is the leaving group; reacting the compound of formula III with Z—S—$R_1^*$, wherein $R_1^*$ is acetyl, and Z is K, Na, or other cation to produce a compound of formula I*: and

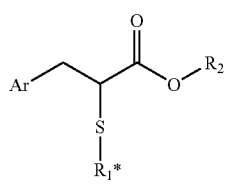

conducting one of the following stereoselective reactions: (a) (1) reacting the compound of formula III with a hydrolase that is stereoselective for the ester; (2) isolating the desired resulting acid; (3) racemizing residual compound of formula III; and (4) conducting at least one additional iteration of steps (a)(1) and (a)(2) with the racemized residual compound of formula III, wherein the reacting with Z—S—$R_1^*$ is conducted with stereoselective inversion of the chiral carbon; or (b) (1) reacting the compound of formula I* with a hydrolase that is stereoselective for the ester; (2) isolating the desired resulting acid; (3) racemizing residual compound of formula I*; and (4) conducting at least one additional iteration of steps b(1) and b(2) with the residual racemized compound of formula I*.

The method may further comprise: crystallizing the compound of formula I* to obtain the compound of formula I* in increased enantiomeric purity. In a preferred embodiment the isomeric purity of the compound of formula I* is at least 98% ee.

The method may further include reacting with a catalytic amount of tetraalkylammonium halide in the racemization steps of a(3) and b(3).

In one preferred embodiment of the method, the halogenating agent is N,N-dibromo-5,5-dimethylhydantoin. In another preferred embodiment the halogenating agent is N,N-dichloro-5,5-dimethylhydantoin.

In a further aspect, the invention provides a method of preparing a compound of formula II:

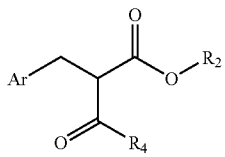

herein $R_2$ and $R_4$ are independently $C_1$ to $C_6$ alkyl, the method comprising: reacting at least five equivalents of $R_4$—C(O)—$CH_2$—C(O)O—$R_2$ with Ar$CH_2$Cl wherein Ar is $C_6$ or $C_{10}$ aromatic group that can be substituted with $C_1$ to $C_6$ alkyl or halo, wherein the reaction is conducted in a solution consisting essentially of the reactants and no more than 1.2 molar equivalents of a base source of sodium or potassium $C_2$ to $C_6$ alkoxide, which can be provided in the corresponding alcohol. In a preferred embodiment the alkoxide concentration in the base source is at least 3 M.

DETAILED DESCRIPTION OF THE INVENTION

This invention relates to the methods of stereoselectively producing desired enantiomers of important intermediates for producing pharmaceuticals.

The invention relates to a method for the enzymatic resolution of aryl and thiosubstituted acids. Additionally, a process for the preparation of the enzyme substrate aryl and thiosubstituted acid derivatives are disclosed.

The methods of the invention are described with reference to formulas I, I*, II and III, as outlined above in the Summary. Ar is $C_6$ or $C_{10}$ aromatic group that can be substituted with H, $C_1$ to $C_6$ alkyl (preferably $C_1$ to $C_3$), trifluoromethyl or halo, $R_5$ is halo or —S—$R_1$, wherein $R_1$ is H or acetyl, and $R_2$ is H or $C_1$ to $C_6$ alkyl (preferably $C_1$ to $C_3$). $R_4$ is $C_1$ to $C_6$ alkyl (preferably $C_1$ to $C_3$). $R_{2*}$ is $C_1$ to $C_6$ alkyl (preferably $C_1$ to $C_3$).

The invention can be described with reference to Scheme 1.

Scheme 1

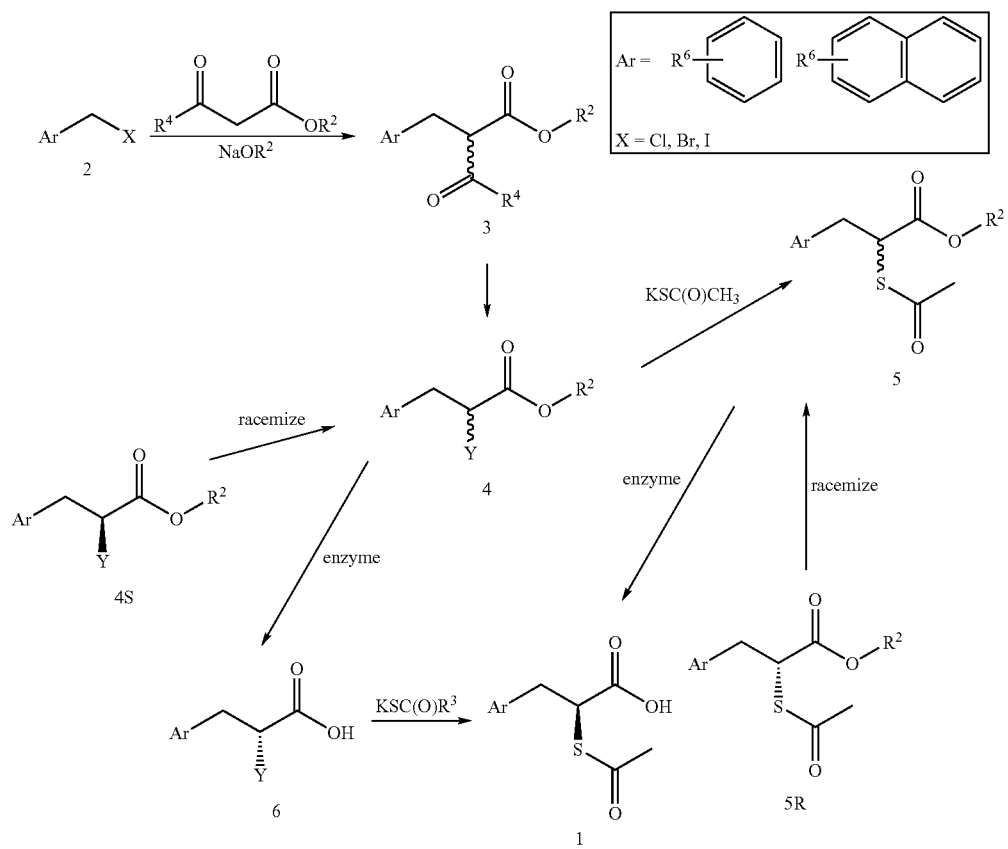

An overall process for preparing, for example, 3-aryl-2-acetylthio-substituted propanoic acids (1) is illustrated in Scheme 1. Initially, alkyl acetoacetates (or any other β-keto esters) are alkylated with benzyl chloride (2) (or substituted analogs thereof) to provide keto esters (3). A halogenation-deacetylation reaction effects the conversion of 3 to the 2-halo-3-arylpropanoic esters (4). Direct treatment of 4 with thioacetate salts furnishes racemic alkyl 2-acetylthio-3-aryl propanoates (5). At this stage, an enzymatic resolution of 5 can be effected. Enantioselective hydrolysis of the ester of 5, for example, provides the S-isomer of acid 1 with excellent enantioselectivity. 1 can be conveniently separated from the unreacted R-ester 5R. The invention also provides for methods for recycling of the unreacted R ester (5R) to provide additional supplies of the racemic substrate for the enzymatic resolution step. In an alternative embodiment of the invention, the enzymatic resolution step is carried out at the stage of the α-halo ester 4. In this case enzymes and reaction conditions are chosen to optimize the enantioselective hydrolysis of the R-halo ester and provide R-halo acid (6). 6 can be displaced with inversion of configuration with a thioacetate salt to provide 1. Again a method is provided for recycling unreacted ester (4S) from the enzymatic resolution step to provide additional racemic substrate for the hydrolysis reaction.

Alkyl 2-aryl methylacetoacetates (3) can be prepared conveniently and in high yield by alkylation of alkyl acetoacetates using optimized conditions that Applicants have developed. Using ethyl acetoacetate and benzyl chloride, Applicants have found that the presence of excess ethyl acetoacetate, without any added solvent (other than the ethanol that is in the concentrated commercially available reagent sodium ethoxide solution) afforded high yields and exclusive mono C-alkylation selectivity. Other methods for conducting this reaction generally require the use of a catalyst (Brandstrom, A. and Junggren, U. *Acta Chem. Scand.* 1969, 23, 2204; Durst, H. D. and Liebeskind, L. *J. Org. Chem.*, 1974, 39, 3271) or use of an inorganic support (Ranu, B. C. and Bhar, S. J. *J. Chem. Soc. Perkin Trans.* 1992, 1, 365). In addition, the preferred methods used in the invention avoids one or more limitations such as the use of toxic materials, laborious and time-consuming procedures, and/or relatively low yields of products. For example, in a non-preferred reaction of ethyl acetoacetate and benzyl chloride, without a phase transfer catalyst, the alkylation reaction provided a modest 25% yield after refluxing in benzene for 8 hours (Durst, H. D. and Liebeskind, L. *J. Org. Chem.*, 1974, 39, 3271). The preferred reaction conditions of the invention allow the utilization of less reactive benzyl chlorides to provide high yields. It is advantageous to use less expensive benzyl chlorides versus more expensive benzylating agents, such as benzyl bromides (and, in general aryl methyl chlorides versus aryl methyl bromides), as starting materials in large scale manufacturing.

Suitable bases for the alkylation reaction include sodium, potassium, or lithium alkoxides, such as sodium ethoxide, $K_2CO_3$ or NaH. The corresponding sodium, potassium, or lithium alkoxides of the alkyl ester are preferred bases for the reaction to avoid the transesterification reactions that can plague reactions of esters. Often a convenient source of alkali metal alkoxide bases are in solutions of the corresponding alcohol that are either commercially available or readily prepared These alkoxides include sodium, potassium, or lithium salts of $C_1$ to $C_6$ alkoxides. Preferably the concentration of this base source solution is at least 3 M. A slight molar excess of base, such as 1.2 molar equivalents relative to the aryl methyl chloride is used.

It can be recognized by those in the art that these reaction conditions are useful for other alkyl β-ketoesters of the formula $R_4$—C(O)—$CH_2$—C(O)O—$R_2$, besides ethyl acetoacetate. These β-ketoesters include compounds where $R_4$ and $R_2$ are independently $C_1$–$C_6$ alkyl, or preferably $C_1$ to $C_3$ alkyl. Moreover, in addition to benzyl chloride other arylmethyl chlorides can be used including $C_6$ or $C_{10}$ alkyl or halo substituted arylmethyl chloride groups. Moreover the aryl moiety can be substituted by H, $C_1$ to $C_6$ alkyl or halo groups. These aryl methyl chloride groups include, for example, benzyl and napthylmethyl chloride analogs. A large molar excess of the alkyl acetoacetate relative to the arylmethyl chloride is preferably used, preferably at least a 5 fold excess. The excess of starting acetoacetate can, for example, be conveniently recovered by fractional distillation under reduced pressure, and reused in the process. The yield of the alkylation reaction is at least 95%, more preferably at least 99%.

Keto ester 3 is converted to α-halo ester 4 using a halogenation/deacetylation sequence. Bromination-deacetylation reaction of ethyl 2-benzylacetoacetate to give 2-bromo-3-benzenepropanoate has been reported using N-halo succinimides. Applicants have discovered that the expensive brominating agent, N-bromosuccinimide (NBS), can be effectively replaced by a cheaper reagent N,N-dibromo-5,5-dimethylhydantoin (DBDMH) in this reaction. In addition to its low price, both bromine atoms are used-in the bromination-deacetylation transformation to further contribute to its cost-effectiveness. A comparable yield can be achieved using DBDMH in the reaction as when NBS is used. The product 4 can be conveniently isolated from the reaction mixture by, for example, vacuum distillation. The yield of the reaction is preferably at least 80%.

Similarly, it can be recognized by those in the art that N,N,-dichloro-5,5-dimethylhydantoin (DCDMH) can replace N-chlorosuccimide in reactions generating the corresponding α-chloro products. The use of chlorinating agent, DCDMH, achieves the same economic advantages of the corresponding brominating agent, DBDMH. Other N-halo-amides, -imides, -thioamides, or -thioimides (including cyclic halo-amides, -imides, thioamides, or thioimides) effective to donate the halo moiety can also be used. Preferred N-halo-amides, -imides, -thioamides, or -thioimides (including cyclic halo-amides, -imides, thioamides, or thioimides) are those including the moiety —C(O)—N(X)—C(O)—N(X)—, where the halo moiety, X, is chloro or bromo.

α-Halo esters 4 can be converted to the α-acetylthio ester intermediate 5 using thioacetate salts. Thioalkanoyl salts containing any cation can be used to effect the transformation including ammonium (including alkylammonium) salts or metal salts. Metal alkali salts such as sodium and potassium salts are preferred salts.

The intermediate ester 5 can be hydrolyzed enantioselectively to furnish the S-acid 1 along with unreacted R-ester 5R using an enzymatic hydrolysis procedure. In one embodiment, the lipase is immobilized on particles of a solid support. Mucor genus derived lipases (such as Lipozyme IM from Novo Nordisk Ltd.) have been found to be particularly well-suited for the hydrolysis reaction with this substrate. Using this enzyme and the optimized reaction conditions found by Applicants, it is possible to obtain enantiomeric excess's (e.e.'s) of, for example, 96% or better with high product yields of, for example, 75% or better (based on the consumed ester).

Besides enzyme selection, other reaction conditions are also important for high enantioselectivity in the enzymatic resolution. The reaction conditions can be altered by several variables including substrate concentration, solvent, pH, and incubation time. As summarized in Table 1, the effects of substrate concentration, solvent, and incubation time on the yield and enantioselectivity of the hydrolysis reaction can be assessed using a screening approach. In addition, the effect of altering the alkyl moiety of the acetoacetate (or any β-keto ester) can be assessed using this same approach. The reactions can be conveniently analyzed by chiral HPLC analysis to determine their conversion ratio and the optical purity of the hydrolyzed product. A typical chiral HPLC uses, for example, a Chiralcel AD (Daicel Chemical Industries) with a mobile phase of hexane:ethanol:trifluoroacetic acid (98:2:0.1%), a flow rate of 1 mL/min and UV detector set to 230 nm.

TABLE 1

| Substrate (Ester) | Substrate Concentration | Solvent | Incubation Time | Conversion ratio | (S) Optical Purity (% ee) |
|---|---|---|---|---|---|
| Ethyl ester | 20 mg/ml | pH 7.0 Buffer | 6 hours | 40 | 74 |
| Ethyl ester | 10 mg/ml | pH 4.0 Buffer | 4.5 hours | 34 | 85 |
| Ethyl ester | 10 mg/ml | 90% t-butanol | 7 hours | 34 | 92 |
| Ethyl ester | 100 mg/ml | pH 4.0 Buffer | 10 hours | 10 | 85 |
| Ethyl ester | 100 mg/ml | 90% t-butanol | 18 hours | 38 | 88 |
| Butyl ester | 10 mg/ml | 90% t-butanol | 10 hours | 52 | 70 |
| Isobutyl ester | 10 mg/ml | 90% t-butanol | 16 hours | 35 | 86 |
| Trifluoroethyl ester | 10 mg/ml | 90% t-butanol | 1 hour | 90 | 20 |
| Ethyl ester | 10 mg/ml | 90% acetonitrile | 40 hours | 42 | 96 |
| Ethyl ester | 10 mg/ml | 90% acetone | 40 hours | 25 | 97 |
| Ethyl ester | 10 mg/ml | 90% Isopropanol | 40 hours | 37 | 94 |

Applicants have discovered that using a solvent mixture of an organic solvent and buffer (or water) in the enzymatic hydrolysis reaction provides better selectivity than buffer alone. The ratio of organic solvent to buffer ranges from 98:2 or 95:5 to 50:50, preferably, 98:2 to 80:20. Applicants have found that in addition to the high yield and high e.e's obtained using the mixture of organic solvent and buffer, use of the solvent mixture also allows recovery of the enzyme without significant loss of hydrolase activity. In other words, the enzyme can be recovered from the reaction mixture, and can be reused for additional hydrolysis batch runs. In one embodiment, the solvent is selected to be effective to produce an enantiomeric excess of the desired enantiomer of the acid of at least 88%, and preserve at least 90% of the enzymatic activity of the lipase. Preferably at least 90% of the enzymatic activity is preserved over four hydrolysis batch cycles. The organic solvents can be acetonitrile; ketones, for example, acetone; or alcohols, for example, t-butanol and isopropanol. Preferred organic solvents include acetonitrile, acetone, and t-butanol.

Buffers useful in the enzymatic reactions of the invention include buffers that have a buffering range of 4 to 8. Useful buffers include, for example, acetate buffers, tetraborate buffers, phosphate buffers, HEPES, Tris-HCl, or citrate buffers. Optimized pH values for this enzymatic resolution are dependent on the particular enzyme used, and are preferably from 4 to 8, and more preferably from 4 to 6. A preferred buffer is a 0.2M sodium acetate buffer with a pH of about 4.

The reaction temperature can be in the range of 5° C. to 70° C., preferably 15° C. to 37° C.

The invention provides a method for the convenient recovery of the enzyme, the acid 1, and the unreacted ester 5R from the hydrolysis reaction. The enzyme is recovered by for example, filtration and washing with a mixture of organic solvent and buffer. The enzyme is suitable for reuse in the hydrolysis reaction. The acid 1 and the unreacted ester 5R can be recovered from the filtrate. The filtrate is concentrated by, for example, vacuum distillation to provide a mixture of the acid 1 and the unreacted ester 5R. The mixture is partitioned between an alkaline aqueous solution and an organic solvent such as methyl t-butyl ether (MTBE). After separation of the layers, the unreacted ester 5R is recovered by concentration of the organic layer. The aqueous solution is acidified and extracted with an organic solvent. This organic extracts are washed with brine and concentrated to furnish the S-acid 1.

In another embodiment of the invention a method is provided for the purification of the crude product 1. The ee of the crude product 1 can be improved by crystallization from a mixture of solvents. The ee of the crude product can be, for example, improved to at least 95%, preferably at least 98%. For example, if the ee of the crude product is 88% the ee can preferably be improved to greater than 99% ee with a 65% yield from the crude product. A preferred crystallization solvent includes a mixture of a $C_1$ to $C_4$ alkyl ether and a $C_5$ to $C_7$ alkane. A particularly preferred solvent includes a mixture of methyl t-butyl ether (MTBE) and heptane.

Re-use of the unreacted ester 5R can be achieved by racemization of 5R to provide additional quantities of the substrate, racemic 5, for the enzymatic hydrolysis. Any method that provides a racemic mixture of 5 can be used for the racemization of 5R including epimerization type reactions and displacement reactions using catalytic amounts of nucleophiles such as halides. Warming a mixture of the recovered 5R and catalytic amounts of a halide salt is a preferred method of racemizing the thioacetate ester. In particular, tetraalkyl halides, such as tetrabutylammonium bromide, are most preferred as catalysts for the racemization step.

In an alternative embodiment of the invention, an enzymatic hydrolysis of the halo acid ester 4 provides an R α-halo acid 6 enantioselectively. This pathway provides a nonracemic chiral intermediate suitable for direct conversion to S α-thioacetate 1. Suitable enzymes and solvents can be screened in the hydrolysis reaction using a screening approach (See Table 2). For example, Subtilisin BPN (from Sigma), Neutral Protease N (from Amano), and Lipozyme IM (from Novo Nordisk) give particularly good results using Applicant's reaction conditions. In one embodiment the lipase is immobilized on particles of a solid support. Suitable solvents for this enzymatic hydrolysis reaction are mixtures of organic solvents and an aqueous buffer. The percentage of the organic solvent in the mixture is preferably in the range of 20 to 95%, more preferably in the range of 30% to 60%. Organic solvents that are useful for this reaction include acetonitrile; ketones, such as acetone and cyclohexanone; cyclic ethers such as tetrahydrofuran and 1,4-dioxane; and alcohols such as t-butanol and isopropanol.

TABLE 2

| Enzyme | Substrate (ester) | Solvent % | Incubation | Conversion Ratio | (R) Optical Purity (% ee) |
|---|---|---|---|---|---|
| Lipase-*Mucor meihei* | Ethyl ester | pH 7.0 buffer | 1 hour | 38 | 68 |
| Lipase-*Mucor meihei* | Ethyl ester | 95% Cyclohexanone | 5 hour | 35 | 80 |
| Protease subtilisin BPN' | Ethyl ester | pH 7.0 buffer | 5 hours | 45 | 75 |
| Protease subtilisin BPN' | Ethyl ester | 30% THF | 4 hours | 46 | 84 |
| Neutral protease *Bacillus subtilis* | Ethyl ester | 30% Acetone | 2 hours | 45 | 80 |
| Lipase-*Mucor meihei* | Butyl ester | 95% Cyclohexanone | 18 hours | 60 | 50 |
| Protease subtilisin BPN' | Butyl ester | 30% THF | 4 hours | 28 | 72 |
| Lipase-*Mucor meihei* | Isobutyl ester | 95% Cyclohexanone | 8 hours | 25 | 70 |
| Protease subtilisin BPN" | Isobutyl ester | 30% THF | 4 hours | 46 | 80 |

The temperature for this hydrolysis reaction is in the range of 5° C. to 70° C., preferably 15° C. to 37° C. The ee of the product 6 is preferably at least 80%.

The enantiopure 6 can then be directly converted with inversion of the α-center to 1 using thioacetate salts using the conditions described above for the racemic α-bromo ester 4.

The invention provides for recycling of the unreacted S α-halo ester 4S from the hydrolysis reaction, similar to the recycling of the α-thioacetyl ester 5R in the first recycling process. Re-use of the unreacted ester 4S can be effected by recovery of and racemization of 4S. The unreacted ester 4S can be conveniently recovered by the same method that was described above for the unreacted α-thioacetate ester 5R. Any method that provides a racemic mixture of additional substrate 4. for the enzyme can be used for the racemization step. These methods include epimerization type reactions and displacement reactions using catalytic amounts of nucleophiles such as halides. Warming a mixture of halo ester 4S and catalytic amounts of a halide salt is a preferred method of racemizing the halo ester ester. In particular, tetraalkyl halides, such as tetrabutylammonium bromide, are most preferred as catalysts for the racemization step.

Note that while the invention has been described with reference to Scheme 1, the various compounds of the formulas set forth in the claims and summary of the invention can be used or made in the processes of the invention. Analogs of the compounds of Scheme 1 required to make the other compounds of the invention shall be recognizable to those of ordinary skill.

The following examples further illustrate the present invention, but of course, should not be construed as in any way limiting its scope.

EXAMPLE 1

Preparation of Ethyl 2-Benzylacetoacetate

To a 1 L 4-necked round bottom flask that was equipped with an overhead stirrer, a condenser, an addition funnel and a temperature-probe, was added 207.3 g of ethylacetoacetate. A solution of sodium ethoxide/ethanol (21 wt. %, 113.1 g) was added at 20–25° C. The reaction mixture was stirred for 15 minutes. Benzyl chloride (39.14 g, 0.3092 mole) was then added through an addition funnel dropwise over 15 minutes. The resulting reaction mixture was heated to 80° C. for 2–3 hours before cooling to room temperature. Water (300 mL) was added to the reaction mixture, and the phases were separated in separatory funnel. The product was extracted with ethyl acetate (250 mL) three times. The combined organic phase was washed with 600 mL of saturated ammonium chloride solution. After drying and evaporation of solvent, the unreacted starting material and product were separated and isolated by fraction distillation under vacuum. The recovered starting material weighed 137.1 g, 82% recovery yield. Product, ethyl 2-benzylacetoacetate, was 64.2 g, 94% yield.

EXAMPLE 2

Preparation of Ethyl 2-Bromo-3-benzenepropanoate with N-Bromosuccinimide

To a 2 L 4-necked round bottom flask that was equipped with an overhead stirrer, an addition funnel, a condenser and a temperature-probe, was added the solution of sodium ethoxide/ethanol (21% wt. %, 161.8 g) at 20–25° C. under nitrogen. Ethyl 2-benzylacetoacetate (103.1 g, 0.454 mole) was added dropwise. The resulting solution was stirred at 20–25° C. for 30 minutes. The reaction mixture was then cooled to −35° C. with a dry ice/acetone bath. N-Bromosuccinimide (NBS; 97.95 g, 0.545 mole) was added portion-wise over 30 minutes. After the addition was over, the reaction mixture was stirred at −35° C. for 1 hr before warming up to 20–25° C. and it was stirred for an additional 2 hrs. The reaction was then quenched with water (400 mL) and ethyl acetate (600 mL) was added. The layers were separated and the product was extracted from aqueous layer with ethyl acetate (400 mL×3). The combined organic layers was washed with saturated sodium bicarbonate twice (400 mL×2), water twice (400 mL×2) and brine (500 mL). After the removal of solvent, the product (crude, 132 g) was distilled under reduced pressure. Ethyl 2-bromo-3-benzenepropanoate (97.7 g) was obtained at yield 83.7%.

EXAMPLE 3

Preparation of Ethyl 2-Bromo-3-Benzenepropanoate with (N,N-Dibromo-5,5-dimethylhydantoin To a 100 mL 3-necked round bottom flask that was equipped with an overhead stirrer, an addition funnel, a condenser and a temperature-probe, was added the solution of sodium ethoxide/ethanol (21% wt. %, 0.81 g) at 20–25° C. under nitrogen. Ethyl 2-benzylacetoacetate (0.48 g, 2.19 mmol) was added dropwise. The resulting solution was stirred at 20–25° C. for 30 minutes. The reaction mixture was then cooled to −35° C. with a dry ice/acetone bath. N,N-Dibromo-5,5-dimethylhydantoin (DBDMH; 0.32 g, 1.09 mmol) was added portion-wise over 30 minutes. After the addition, the reaction mixture was stirred at −35 ° C. for 1 hr before warming up to 20–25° C. and it was stirred for an additional 1 hr. The reaction was then quenched with water (3 mL) and ethyl acetate (3 mL) was added. The layers were separated and the product was extracted from the aqueous layer with ethyl acetate (5 mL). The combined organic layers was washed with saturated sodium bicarbonate (5 mL), and brine (5 mL). After the removal of solvent, ethyl 2-bromo-3-benzenepropanoate (0.46 g) was obtained at yield 81%.

EXAMPLE 4

Enzymatic Production of Optically Active 2-Acetylthio-3-Benzenepropanoic Acid

Ten (10.0) or 100.0 mg of racemic ethyl 2-acetylthio-3-benzenepropanoate was added to 1000 µl of 90% tert-butanol and 10% 200 mM sodium acetate buffer (pH 4.0) which contained 10 mg of immobilized lipase from *Mucor meihei* (Novo). The glass vessel was tightly capped and stirred for 0–40 hours at room temperature. Thirty µl aliquots were-removed to ascertain conversion and optical purity. The aliquots were analyzed using an chiral HPLC column (Chiralcel AD, Daicel Chemical Industries) with a mobile phase of hexane:ethanol:trifluoroacetic acid 98:2:0.1%. The flow rate is 1 ml/minute and detection was at 230 nm. This experiment was also performed in 90% acetonitrile, acetone, and isopropanol as described above. Other racemic esters were also evaluated: butyl, isobutyl, and trifluoroethyl. The results described in Table 1 (above) were obtained.

EXAMPLE 5

Enzymatic Resolution of Ethyl 2-Acetylthio-3-benzenepropanoate

To a 500 mL 3-necked round bottom flask that was equipped with an overhead stirrer and a syringe pump, was added the solution of 0.2M NaOAc (60 mL, pH 5), tBuOH (240 mL), and then the immobilized lipase enzyme from *Mucor meihei* (Novo) (3.0 g). Ethyl 2-acetylthio-3-benzenepropanoate (30.0 g, diluted with 15 mL of solvent) was added over 9 hrs using a syringe pump. After the addition, the reaction mixture was stirred at rt for 13 hrs. The enzyme was filtered off, and washed with tBuOH and 0.2M NaOAc (2×20 mL, 80:20 v/v). The solvent in the filtrate was removed under reduced pressure. The concentrated filtrate was mixed with 200 mL MTBE and 150 mL water, and adjusted to pH 7.5 by 2 N NaOH. The layers were separated and the ester was extracted from the aqueous layer with MTBE (3×100 mL). After the removal of solvent, ethyl 2-acetylthio-3-benzenepropanoate (19.2 g) was recovered, at a 63.9% yield. To the aqueous phase at pH 7.5 was added 200 mL MTBE, and the pH was adjusted to pH 2 by 10% $H_2SO_4$. The layers were separated and the acid was extracted from aqueous layer with MTBE (3×100 mL). The combined organic layers were washed with brine (2×150mL), and partially distilled at 55° C. under ambient pressure. After further removal of solvent, (S)-2-acetylthio-3-benzenepropanoic acid (8.3 g) was obtained at a 31.1% yield (ee:88.4%).

EXAMPLE 6

Crystallization of (S)-2-Acetylthio-3-benzenepropanoic Acid

The crude (S)-acetylthio-3-benzenepropanoic acid (8.29 g; 88.4%), obtained after solvent removal, was dissolved in MTBE (4 mL, 1.4 mL/g). The solution of acid in MTBE was then heated to 45° C. Heptane (25 mL) was added dropwise to the warm solution until cloudy. The slurry was seeded with (S)-acetylthio-3benzenepropanoic acid crystal, and slowly cooled to r.t. without agitation. The addition of heptane was continued (15 mL) with agitation over 30 min. The solid (5.5 g) was collected via vacuum filtration after chilling in an ice/water bath, and washed with cold heptane. The purified (S)-acetylthio-3-benzenepropanoic acid was assayed by HPLC to determine the purity and % ee (purity 98.2% and ee 98.7% at a 66% yield).

EXAMPLE 7

Racemization of Unreacted Ethyl 2-Acetylthio-3-benzenepropanoate with Tetrabutylammonium Bromide To a 250 mL 3-necked round bottom flask that was equipped with an overhead stirrer, a condenser and a temperature probe, was added the solution of ethyl 2-acetylthio-3-benzenepropanoate (47.3 g, R-acid:S-acid=1:1.7) and tetrabutylammonium bromide (6.4 g, 10 mol %). The ester/bromide mixture was heated at 50° C. for 2.5 hrs. The bromide salt was filtered off, and washed with MTBE (3×100 mL). After solvent removal under reduced pressure, the racemized ethyl 2acetylthio-3-benzenepropanoate (47.6 g, R-acid:S-acid=1:1.2) was recovered in essentially 100% yield with some residual solvent.

DEFINITIONS

The following terms shall have, for the purposes of this application, the respective meanings set forth below.

Halo. Halo refers to fluoro, chloro, bromo, and iodo. Preferably, the halo moieties are chloro or bromo.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods can be used and that it is intended that the invention can be practiced otherwise than as specifically described herein. Accordingly, this invention includes all modifications encompassed within the spirit and scope of the invention as defined by the claims that follow.

What is claimed is:

1. A method of preparing a compound of formula II:

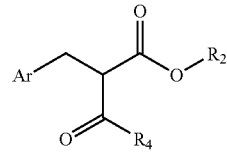

(II)

wherein $R_2$ and $R_4$ are independently $C_1$ to $C_6$ alkyl, the method comprising:

reacting at least five molar equivalents of $R_4$—C(O)—$CH_2$—C(O)O—$R_2$ with one molar equivalent of $ArCH_2Cl$ wherein Ar is $C_6$ or $C_{10}$ aromatic group that can be substituted with $C_1$ to $C_6$ alkyl or halo, wherein the reaction is conducted in a solution consisting essentially of the reactants and no more than 1.2 molar equivalents of a base source of sodium, potassium, or lithium $C_2$ to $C_6$ alkoxide, which can be provided in the corresponding alcohol.

2. The method of claim 1, wherein the alkoxide concentration in the base source is at least 3 M.

3. The method of claim 1, wherein in the compound of formula II Ar is phenyl and $R^2$ and $R^4$ are each methyl.

4. The method of claim 1, wherein $R_4$—C(O)—$CH_2$—C(O)O—$R_2$ — is ethyl acetoacetate, $ArCH_2Cl$ is benzylchloride and the compound of formula II is

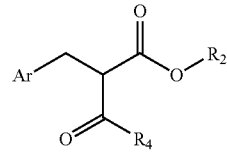

(II)

5. The method as defined in claim 1 wherein $R_4$—C(O)—$CH_2$—C(O)O—$R_2$ is ethyl acetoacetate.

6. The method as defined in claim 1 wherein $ArCH_2Cl$ is benzyl chloride.

7. The method as defined in claim 1 wherein the base source is sodium ethoxide in ethanol.

8. The method as defined in claim 1 wherein $R_4$—C(O)—$CH_2$—(O)O—$R_2$ is ethyl acetoacetate, $ArCH_2Cl$ is benzyl chloride and the base source is sodium ethoxide in ethanol.

9. The method as defined in claim 1 wherein the compound formed is ethyl-2-benzyl acetoacetate.

10. The method as defined in claim 1 wherein $ArCH_2Cl$ is naphthylmethyl chloride.

* * * * *

UNITED STATES PATENT AND TRADEMARK OFFICE
CERTIFICATE OF CORRECTION

PATENT NO. : 7,141,694 B2  Page 1 of 1
APPLICATION NO. : 10/625403
DATED : November 28, 2006
INVENTOR(S) : Jingyang Zhu et al.

It is certified that error appears in the above-identified patent and that said Letters Patent is hereby corrected as shown below:

Claim 4, column 14, line 45, replace the structure with the following:
--
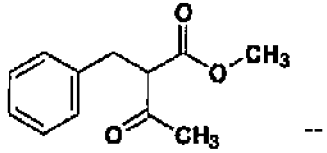
--

Please delete claim 10, cancelled in previous amendment.

Signed and Sealed this

Seventh Day of August, 2007

JON W. DUDAS
*Director of the United States Patent and Trademark Office*